United States Patent [19]

Sepetka

[11] Patent Number: 5,228,453
[45] Date of Patent: Jul. 20, 1993

[54] CATHETER GUIDE WIRE

[75] Inventor: Ivan Sepetka, Redwood City, Calif.

[73] Assignee: Target Therapeutics, Inc., Fremont, Calif.

[21] Appl. No.: 952,206

[22] Filed: Sep. 28, 1992

Related U.S. Application Data

[63] Continuation of Ser. No. 696,585, May 7, 1991, abandoned.

[51] Int. Cl.⁵ .............................................. A61B 5/00
[52] U.S. Cl. ...................................... 128/772; 128/657
[58] Field of Search .................. 128/657, 772; 604/95, 604/164, 285

[56] References Cited

U.S. PATENT DOCUMENTS

| | | | |
|---|---|---|---|
| 4,003,369 | 1/1977 | Heilman et al. | 128/772 |
| 4,719,924 | 1/1988 | Crittenden et al. | 128/657 |
| 4,884,579 | 12/1989 | Engelson | 128/657 |
| 4,922,924 | 5/1990 | Gambale et al. | 128/657 |
| 4,964,409 | 10/1990 | Tremulis | 128/657 |
| 5,065,769 | 11/1991 | de Toledo | 128/772 |
| 5,069,217 | 12/1991 | Fleishhacker | 128/772 |
| 5,129,890 | 7/1992 | Bates et al. | 128/772 |

*Primary Examiner*—Max Hindenburg
*Attorney, Agent, or Firm*—Morrison & Foerster

[57] ABSTRACT

A catheter guide wire comprising: a flexible, torqueable proximal wire section, a more flexible intermediate section with a flexible polymer tube covering, and a most flexible distal end section. A helical ribbon coil is wrapped about the intermediate core segment between the wire core and the polymer tube covering to increase radiopacity and improve torque transmission while retaining flexibility.

8 Claims, 1 Drawing Sheet

CATHETER GUIDE WIRE

This application is a continuation of application Ser. No. 07/696,585, filed May 7, 1991, now abandoned.

DESCRIPTION

1. Technical Field

This invention is in the general field of surgical instruments and relates specifically to guide wires that are used in cardiovascular and endovascular procedures to facilitate the placement of catheters within the vasculature of patients.

2. Background

The general procedure for placing catheters within vessels is to track a guide wire through the vessel to the desired position and advance the catheter over the guide wire. Guide wires are required because the catheters themselves do not have sufficient column strength or torsional strength to be able to be tracked or steered through the vessel. See, for instance, U.S. Pat. No. 4,884,579.

Several types of guide wires for use in catheter placement have been proposed. The simplest type of wire has a preferred diameter of between about 0.20–1.0 mm. The distal end of the wire may be provided with a bent tip which can be oriented, by means of a guide structure at the proximal end, to guide the wire along a selected vascular path. Ideally, torque transmission should be controlled, such that a selected wire rotation at the wire's proximal end produces a corresponding rotation of the distal end. Further, radiopacity is desired such that a physician may see over the entire vasculature accessed by the guide wire.

The present invention is an improvement on the guide wire assembly described in U.S. Pat. No. 4,884,579. The prior invention describes a catheter guide wire with three sections with progressively greater flexibility and sliding properties: 1. A semi-rigid, torqueable proximal wire section that is between about 50–250 cm in length, formed of a proximal wire core segment having an outer diameter of between about 0.25–1.0 mm; 2. A more flexible intermediate section that has a length between about 20–60 cm and is formed from an intermediate wire-core segment having a reduced diameter of between about 0.10–0.50 mm, and a low-friction, flexible polymer tube covering which encases the intermediate core segment; and 3. A most distal end section with a length between about 1–10 cm and formed from a distal wire core segment having a reduced diameter of between about 0.05–0.15 mm, and a flexible sleeve covering the distal end segment and providing column strength thereto.

A primary object of the present invention is the improvement of the torque transmission and radiopacity of the above described invention.

DISCLOSURE OF THE INVENTION

The invention is an improvement to U.S. Pat. No. 4,884,579 which describes a catheter guide wire for use within a patient's vasculature comprising in combination:

(a) a flexible, torqueable proximal wire section, (b) a more flexible intermediate section formed from an intermediate wire-core segment having a flexible polymer tube covering which encases the intermediate core segment, and (c) a most flexible distal end section formed from a distal wire core segment with a helical coil covering the distal end segment and providing column strength thereto.

The improvement comprises a radiopaque helical ribbon coil wrapped about the intermediate core segment between the intermediate wire core and the flexible polymer tube covering. This improvement serves to increase radiopacity and improve torque transmission while retaining flexibility.

BRIEF DESCRIPTION OF THE DRAWING

In the drawing.

Like parts are referred to by the same reference numerals in the figures.

MODES FOR CARRYING OUT THE INVENTION

Figure 1:
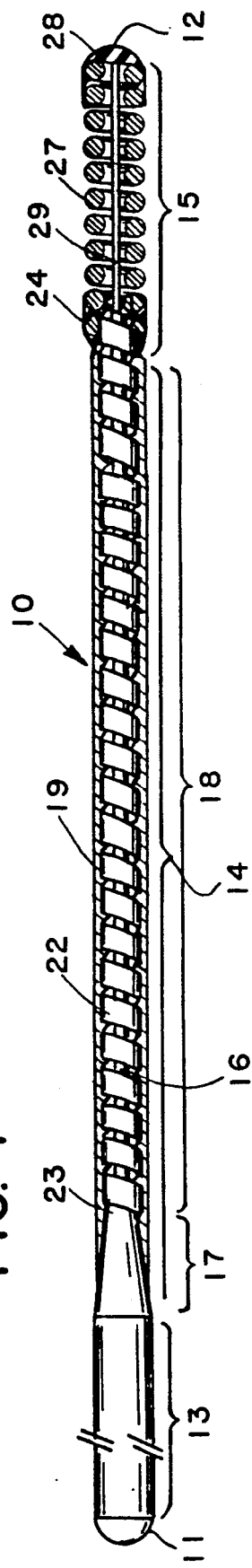
FIG. 1 shows fragmentary portions of a guide wire constructed according to one embodiment of the invention.

FIG. 1 shows a guide wire generally designated 10, constructed according to one embodiment of the invention. The wire is a flexible torqueable wire having an overall length of about 70–300 cm between its proximal and distal ends 11 and 12, respectively, and a maximum outer diameter of between about 0.20–1.0 mm. The major portion of the wire is a flexible proximal section 13 whose overall length ranges from about 50–250 cm. This section is followed by a more flexible intermediate section 14 having a length between about 20–60 cm and a most flexible distal end section 15 whose length is between about 1–10 cm.

A wire core 16 in the guide wire 10 is formed of a flexible, torqueable wire filament material, such as stainless steel. The diameter of the wire core, at its maximum, is between about 0.20–1.0 mm. The segment of the core forming proximal section 13 of guide wire 10 has a substantially uniform diameter along its length, and corresponds to the maximum diameter of the core, i.e., between 0.20–1.0 mm.

Within the intermediate section 14 of the wire, the core is tapered from the proximal-section diameter down to a reduced diameter which is preferably about 0.10–0.50 mm and between about 10%–50% of the diameter of the core's proximal segment 13. Thus, for example, where the proximal section core diameter is 0.46 mm, the core tapers to a minimum of between about 0.05–0.23 mm. The length of tapered segment 17 is typically between about 10%–50% that of reduced-diameter segment 18, and the two segments together make up the length of the intermediate wire section 14, i.e., about 20–60 cm.

The wire core 16 of intermediate section 14 is covered along its length by a flexible polymer covering 19. The major function of covering 19 is to provide a low-friction surface along intermediate section 14, and more particularly, a surface which has less friction than the surface of adjacent distal segment 15 and proximal segment 13 (the wire core itself). Covering 19 preferably also functions to provide column support to the reduced-diameter core of the intermediate section, 18, to reduce the tendency of this section to buckle under axial compression.

Covering 19 is preferably formed of a polymer, such as TEFLON ™, polyolefin, or polyurethane which can be bonded or otherwise tightly affixed to the core wire, and which itself has a low-friction surface, or can be coated with a low-friction surface. Other suitable coverings include a tube formed from virtually any polymer having exposed hydrogens, such as polyester, polyolefins, polycarbonate, polyvinylchloride, latex or silicon rubber, polystyrene, and polyacrylics, and a surface coating formed of a highly hydrophilic, low-friction polymer, such as polyvinylpyrrolidone (PVP), polyethyleneoxide, or polyhydroxyethylmethacrylate (polyHEMA) or copolymers thereof.

Beneath polymer covering 19, a ribbon of radiopaque metal 22, such as platinum, gold, tungsten, or their alloys is wound around the wire core 16. As shown, the ribbon coil 22 extends from tapered segment 17 of intermediate section 14 at junction 23, to the distal junction 24 of intermediate section 14. The ribbon coil 22 has a thickness of about 0.015 to 0.050 mm, preferably about 0.025 mm and a width of about 0.050 to 0.130 mm, preferably about 0.075 mm. There are approximately 5 to 15 complete turns of ribbon per millimeter of wire core, and preferably about 10 complete turns of ribbon per millimeter of wire core.

The distal section 15 of guide wire 10 is fully or partially encased in flexible sleeve 27. Sleeve 27 shown in FIG. 1 is a soft, flexible helical coil which is formed conventionally, e.g., as a winding of radiopaque wire strand, such as platinum, gold, or tungsten strand. The wire strand has a diameter of about 0.050 to 0.100 mm and preferably about 0.075 mm. As shown, sleeve 27 extends from junction 24 to distal end 12 of guide wire 10. Attachment of the sleeve 27 to wire core 16 is preferably by two or three solder or weld joints, one at proximal junction 24 and a second at rounded distal junction 28.

In addition to providing a mechanism for wire bending near wire tip 12, sleeve 27 also gives distal section 15 of guide wire 10 increased column strength (in the axial direction), and reduces the chance of buckling in this section with axial compression. At the same time, the combined flexibility of reduced diameter core 29 and sleeve 27 are compatible with a series of sharp bends, as the wire is moved through a patient's vasculature. Rounded joint 28 at the end of guide wire 10 acts to shield vessel walls from the sharp end of wire core 16. Further, the distal section of the wire, 15, with the associated sleeve 27, provides the section with a higher frictional coefficient than that of the adjacent intermediate section, 14. The higher-friction surface in this distal section, 15, functions specifically, during a catheter placement operation, to help anchor distal section 15 against a vessel wall at a vessel junction.

Distal wire core 29 has a substantially uniform cross-section. The core may be cylindrical with diameter of between 0.05 and 0.15 mm or flattened with a rectangular cross-section dimensioned 0.025 mm by 0.075 mm. The wire core has a tapered section at junction 24 that covers between about 10–50% of the core's distal segment.

Figure 2:
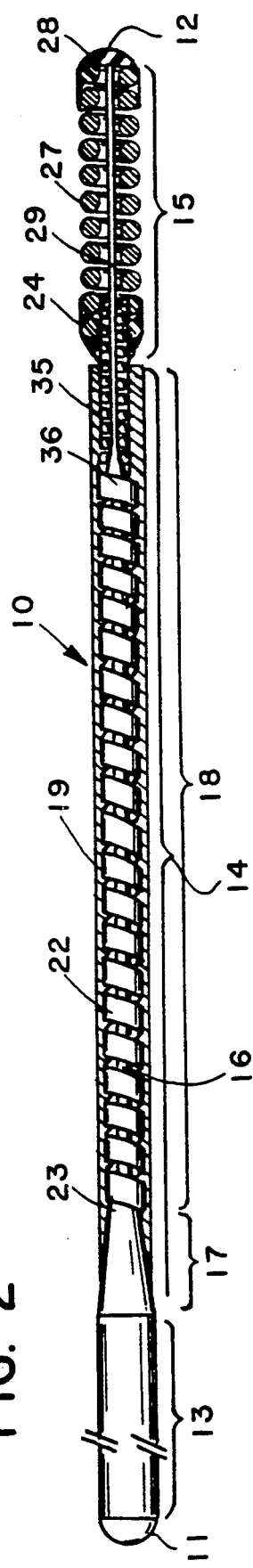
FIG. 2 shows fragmentary portions of a guide wire constructed according to another embodiment of the invention.

FIG. 2 is another embodiment of the invention that is essentially the same as FIG. 1 except for the replacement of a portion of helical ribbon coil 22 with inner wire coil 35. At the distal end of helical ribbon coil 22, there is a soft flexible helical coil 24 which is formed conventionally, e.g., as a winding of radiopaque wire strand, such as platinum, gold or tungsten. As shown, coil 35 extends from helical ribbon coil 22 at junction 36 to the proximal end of distal segment 15 at junction 24. This inner coil 35 serves as an anchor point for the distal end of flexible helical coil 22 and also as an anchor point for the polymer covering 19 on intermediate core section 14.

I claim:

1. In a catheter guide wire for use within a patient's vasculature comprising in combination:
   (a) a semi-rigid, torqueable proximal wire section,
   (b) a more flexible intermediate section formed from an intermediate wire-core segment having a flexible polymer tube covering which encases the intermediate core segment, and
   (c) a most flexible distal end section formed from a distal wire core segment with a helical coil covering the distal end segment and providing column strength thereto,
   the improvement comprising a radiopaque helical ribbon coil wrapped about the intermediate core segment between the intermediate core segment and the flexible polymer tube covering so to improve torque transmission and increase radiopacity of the intermediate section over that of the bare intermediate core segment without substantially increasing its stiffness.

2. The guide wire of claim 1 wherein the ribbon coil is formed from a radiopaque metal selected from the group consisting of platinum, gold, tungsten and their alloys.

3. The guide wire of claim 1 wherein the ribbon coil is a tightly wound coil with a thickness of about 0.015 to 0.050 mm and a width of about 0.050 to 0.130 mm, which extends from the proximal wire section of the guide wire to the junction of the distal wire core segment.

4. The guide wire of claim 1 wherein:
   (a) the flexible, torqueable proximal wire section has an outer diameter of between about 0.25–0.10 mm, and
   (b) the intermediate wire core segment has a reduced diameter of between about 0.10–0.50 mm, and
   (c) the distal wire core segment has a reduced cross-sectional area.

5. The guide wire of claim 4 wherein the distal wire core segment is cylindrical and has a diameter of between about 0.05 and 0.15 mm.

6. The guide wire of claim 4 wherein the distal wire core segment is rectangular with cross-sectional dimensions of 0.025 mm by 0.075 mm.

7. The guide wire of claim 1 wherein:
   (a) the flexible, torqueable proximal wire section has an outer diameter of between about 0.25–0.50 mm, and
   (b) the intermediate wire core segment has a reduced diameter of between about 0.10–0.20 mm, and
   (c) the distal wire core segment has a reduced diameter of between about 0.05–0.13 mm.

8. In a catheter guide wire for use within a patient's vasculature comprising in combination:
   (a) a flexible, torqueable proximal wire section,
   (b) a more flexible intermediate section formed from an intermediate wire-core segment having a flexible polymer tube covering which encases the intermediate core segment, and
   (c) a most flexible distal end section formed from a distal wire core segment with a helical coil covering the distal end segment and providing column strength thereto, the improvement comprising a radiopaque helical ribbon coil wrapped about the intermediate core segment between the intermediate core segment and the flexible polymer tube covering so to improve torque transmission and increase radiopacity of the intermediate section over that of the bare intermediate core segment without substantially increasing its stiffness and wherein a platinum helical coil wrapped around the proximal end of the distal section serves as an anchor point for the proximal end of the distal helical coil and the anchor point for the distal end of the flexible polymer tube covering which encases the intermediate core segment and the helical ribbon coil.

* * * * *